(12) United States Patent
Shalman (10) Patent No.: US 7,341,556 B2
(45) Date of Patent: Mar. 11, 2008

(54) ENDOSCOPE WITH CLEANING OPTICS (75) Inventor: Michael Shalman, Beer Sheva (IL)

(73) Assignee: M.S. Vision Ltd., Ashkelon (IL)

( * ) Notice: Subject to any disclaimer, the term of this patent is extended or adjusted under 35 U.S.C. 154(b) by 250 days.

(21) Appl. No.: 10/480,170

(22) PCT Filed: Jun. 3, 2002

(86) PCT No.: PCT/IL02/00429

§ 371 (c)(1),
(2), (4) Date: Jun. 21, 2004

(87) PCT Pub. No.: WO02/100238

PCT Pub. Date: Dec. 19, 2002

(65) Prior Publication Data
US 2004/0220452 A1 Nov. 4, 2004

(30) Foreign Application Priority Data
Jun. 11, 2001 (IL) .................................. 143682

(51) Int. Cl.
A61B 1/015 (2006.01)
A61B 1/12 (2006.01)

(52) U.S. Cl. ...................... 600/157; 600/158; 600/159; 600/169; 600/187

(58) Field of Classification Search ........ 600/156–159, 600/169, 187
See application file for complete search history.

(56) References Cited

U.S. PATENT DOCUMENTS

| | | |
|---|---|---|
| 3,863,624 A | 2/1975 | Gram |
| 3,889,682 A | 6/1975 | Denis et al. |
| 3,903,877 A | 9/1975 | Terada |
| 3,980,078 A | 9/1976 | Tominaga |
| 4,063,556 A | 12/1977 | Thomas et al. |
| 4,178,932 A | 12/1979 | Ryder et al. |
| 4,497,550 A | 2/1985 | Ouchi et al. |
| 4,509,507 A | 4/1985 | Yabe |
| 4,548,197 A | 10/1985 | Kinoshita |
| 4,667,655 A | 5/1987 | Ogiu et al. |
| 4,870,975 A | 10/1989 | Cronk et al. |
| 4,971,034 A | 11/1990 | Doi et al. |
| 5,183,031 A | 2/1993 | Rossoff |
| 5,191,878 A * | 3/1993 | Iida et al. ................... 600/157 |
| 5,193,533 A | 3/1993 | Body et al. |
| 5,339,800 A * | 8/1994 | Wiita et al. ................. 600/109 |
| 5,431,152 A | 7/1995 | Flam et al. |
| 5,575,756 A | 11/1996 | Karasawa et al. |
| 5,630,795 A * | 5/1997 | Kuramoto et al. ............ 604/30 |
| 5,637,075 A | 6/1997 | Kikawada |
| 6,106,458 A | 8/2000 | Ha |

(Continued)

Primary Examiner—John P. Leubecker
(74) Attorney, Agent, or Firm—Nixon & Vanderhye P.C.

(57) ABSTRACT

The instrument has an original cleaning system, which includes a gas nozzle supplying a gas jet onto the optical surface under high pressure. This pressure is sufficient to enable the gas jet to be a single cleaning means for cleaning the optical surface in all clinical instances. A safety means prevents the patient's internal organs from barotrauma by the gas jet and includes a gas jet catcher and a suction pump of ejection type. The latter is arranged in the instrument's handle and can be used also for the removal of abundant secretions or body's small particles from the patient's cavity. Besides, the gas jet and the suction pump along with a control means form the system for pressure control within the patient's cavity.

62 Claims, 4 Drawing Sheets

U.S. PATENT DOCUMENTS

| | | |
|---|---|---|
| 6,354,992 B1 | 3/2002 | Kato |
| 6,409,657 B1 * | 6/2002 | Kawano .................... 600/157 |
| 6,447,446 B1 * | 9/2002 | Smith et al. ................ 600/157 |
| 6,558,317 B2 * | 5/2003 | Takahashi et al. .......... 600/158 |
| 2002/0173699 A1 * | 11/2002 | Becker et al. ............... 600/114 |

* cited by examiner

ENDOSCOPE WITH CLEANING OPTICS

FIELD OF THE INVENTION

This invention relates generally to medical instruments for the operation in patient's body cavity requiring the visualization of internal organs. More particularly, it relates to intubation laryngoscopes, bronchoscopes, endoscopes of various applications, vacuum curettage devices, and the like.

BRIEF DESCRIPTION OF THE PRIOR ART

All the endoscope systems applied for the visualization of patient's internal organs comprise at least one endoscope distal optical member disposed at the endoscope distal end. The dirtying of the distal optical member surface with patient's secretions such as blood, mucus, vomit, fat creates significant difficulties for the internal organs visualization. These problems arise in the cases of bleeding an esophageal and gastrointestinal lesions, bleeding or copious secretions in airways, colonoscopy for poorly prepared patient, hysteroscopy during and after curettage and the like. Another problem obstructing the visualization is fogging the distal optical surface due to the temperature difference between the optical surface and patient's cavity. Therefore, cleaning the distal optical surface from patient's secretions and fog is one of the most important problems of current endoscope developments.

U.S. Pat. Nos. 4,509,507, 4,548,197, 4,667,655 disclose endoscope devices comprising an air supply pipe and a water supply pipe disposed within an endoscope housing and connected with a distal nozzle through which air and water are alternately supplied in front of a distal optical surface (viewing window). There is also a complex system for supply and control air and water including a pump means, a control means, a water reservoir, and communications, disposed beyond the endoscope device. The disadvantage of these endoscopes is low effectiveness of optical surface cleaning from very adhesive substances such as blood, mucus, fat due to low air pressure and the direction of air/water flow, which does not collide with the optical surface and, therefore, cannot sweep off the dirt. The supply of air/water flow of sufficient pressure is impossible, since this leads to barotrauma of patient internal organs by air/water jet. Moreover, the internal organ barotrauma also can be caused by internal pressure during the operation in closed body cavity. The devices do not have any means for the removal of excessive air/water from body cavity or for the dissipation of air/water jet. Another disadvantage is excessive complexity and manufacturing cost of the endoscope system due to the dual (air and water) cleaning system and cumbersome supply and control system disposed beyond the endoscope device. Another disadvantage is the arrangement of air/water nozzle in front of the optical surface (see U.S. Pat. Nos. 4,509,507, 4,667,655) restricting the vision field of the optical surface.

U.S. Pat. No. 3,903,877 discloses an endoscope device and additional equipment arranged beyond the endoscopic device. The endoscopic device comprises air and water pipes for alternate supply air and water to the distal optical surface through a nozzle. Also, there are the pump and control means providing the alternate supply of air and water to the nozzle and disposed beyond the endoscope device. Moreover, there is a suction port at the endoscope device distal end and a suction pump disposed beyond the endoscope device. The endoscope distal end is provided with a rubber barrier ring around the nozzle, distal optical surface and suction port. The disadvantage of this patent is very cumbersome and expensive design due to the dual cleaning system including the numerous equipment disposed outside the endoscope device. The presence of the suction means and circular rubber barrier lowers the danger of internal organ barotrauma. However, upon sufficient air/water high pressure, the suction means and the barrier do not create a catcher completely able to catch air/water jets and to exclude deflection thereof towards patient internal organs, thus, barotrauma may occur. Consequently, the capability of the effective cleaning of the optical surface is restricted. Moreover, during water supply, the suction means cannot only remove water from a body cavity. Inevitably, it also sucks in air creating an undesirable (and dangerous) vacuum in the body cavity. Another disadvantage is the relatively great duration of the cleaning process consisting of washing the distal surface and successively drying it by air.

U.S. Pat. No. 3,980,078 discloses an endoscope device having a nozzle supplying air and water to the distal optical surface, a suction pipe with a distal suction port, a distal circular hood, supply and suction pump means and control means disposed beyond the device. As distinct from U.S. Pat. No. 3,903,877, air and water are transferred to the nozzle with only one pipe. This somewhat simplifies the tubing, but complicates the supply control system. Moreover, there is a circular gap between the distal circular hood and endoscope distal end. This gap is communicated with the suction port to improve water removal from the body cavity. On the other hand, the gap decreases the vacuum in the path of airflow going out of the nozzle and thereby lowers the possibility of its catch and removal. Generally, U.S. Pat. Nos. 3,903,877 and 3,980,078 have the same disadvantages above noted for U.S. Pat. No. 3,903,877.

Thus, the common disadvantages of the endoscope systems with cleaning optics are: their excessive complexity caused by dual (gas and liquid) cleaning systems and cumbersome and expensive pump and control means disposed outside the endoscope device; low cleaning effectiveness due to low pressure of cleaning fluid (gas and liquid); the absence of effective means for catching and removing the cleaning flow; the absence of reliable control means allowing to adjustment of the pressure in the body cavity required for surgical operations.

U.S. Pat. No. 4,497,550 discloses "Device for preventing the observing objective lens window of an endoscope from collecting moisture by directing a small flow of air over the front surface of the observing objective lens window to form a layer of air which has the same temperature as the ambient atmosphere". The device comprises only one supplying gas channel and one nozzle and prevents the distal optical surface from fogging. However, the device cannot provide cleaning of the optical surface from patient secretion due to low air pressure. The device does not comprise any means preventing patient internal organs from barotrauma. Therefore, its air pressure cannot be increased up to the value sufficient for effective cleaning the optical surface.

Attempted cleaning of the distal optical surface in laryngoscopes is disclosed by U.S. Pat. Nos. 5,431,152 and 5,183,031. In both cases, there is an oxygen channel supplying oxygen to the zone of the distal optical surface. However, this oxygen supply cannot effectively clean the optical surface due to the low oxygen pressure and the absence of special oxygen flow directing towards the optical surface. It is impossible to apply sufficient oxygen pressure here because the oxygen flow is directed distally and can cause the barotrauma of patient internal organs. The main object of such oxygen supply is the partial oxygenation of the patient.

It should be noted, that the laryngoscopes with high pressure oxygen (≈50 psig) are applied in medical practice for high pressure jet ventilation (see U.S. Pat. Nos. 5,193,533 and 6,106,458). However, the application of high pressure oxygen for cleaning the optical surface is not disclosed in the prior art.

U.S. Pat. No. 4,971,034 discloses "Body Cavity Pressure Adjusting Device" comprising a suction mechanism, gas sending mechanism, pressure and vacuum pipes, and pressure control system. The device is adapted to be used with an endoscope and designed for the adjustment of required pressure in the body cavity. A main disadvantage of the device is that its application with the endoscope is a very cumbersome, expensive, and inconvenient combination including suction and pressurized gas supply means, pressure control system, vacuum and pressure pipes, as well as an endoscope cleaning system with identical equipment.

The vacuum curettage devices are disclosed by U.S. Pat. Nos. 3,863,624, 3,889,682, 4,063,556, 4,178,932, 4,870,975. They include: a cannula (or curette) communicated with a vacuum pump, which is disposed beyond the curettage device; a valve for selective application of the vacuum to the cannula; a reservoir for the collection of blood, body solid particles and the like; a filter partition separating the reservoir from the vacuum pump. The disadvantage of known curettage devices is the absence of a visualization means eliminating the capability of operative estimate of curettage results. Practically, the curettage procedure is performed blindly. This worsens the quality of the procedure, leads to patient traumatization and successive complications, and extends the operation duration. The application of the visualization means immediately in the curettage device is hampered due to very significant dirtying of the optical surface by curettage products. Another disadvantage of the curettage devices is the arrangement of the vacuum pump beyond the curettage device. This increases the number of communication, heightens the manufacturing cost of the curettage system, and is inconvenient in the operation.

SUMMARY OF THE INVENTION

The object of the present invention is to provide an endoscope with the complete visualization of patient's internal organs even in the most awkward cases.

Another object of the present invention is to provide cleaning of the endoscope distal optical surface only by means of gas jet.

Another object of the present invention is to entirely prevent a patient's internal organs from barotrauma.

Another object of the present invention is to simplify the endoscope design and to lower its manufacturing cost.

Another object of the present invention is to reduce the general duration of an endoscopy procedure.

Another object of the present invention is to improve the convenience of user operation.

Another object of the present invention is to extend the endoscope functional properties, specifically, to provide its capability to serve as a means for body cavity pressure adjusting.

Another object of the present invention is to extend the endoscope applicability including the possibility of its application in laryngoscopes, bronchoscopes, vacuum curettage devices and the like.

The above noted objects are accomplished by an endoscope system, comprising: an elongated endoscope housing, an optical channel with a distal optical surface, a cleaning system for cleaning the optical surface comprising a pressurized gas supply channel connected with a pressurized gas source and having an outlet nozzle at a housing distal end. The outlet nozzle is directed towards the optical surface so that a gas jet going out of the nozzle touches the optical surface, cleaning it. The pressure value of gas supplied to the outlet nozzle is sufficient to enable the gas jet to completely clean the optical surface from any patient secretions and to be a single means for cleaning the optical surface. All the components of the cleaning system are disposed inside of the endoscope device, with the exception of the pressurized gas source disposed beyond the endoscope. There is also a safety means preventing barotrauma of the patient internal organs by the gas jet.

Using the gas jet as a single means for cleaning the optical surface significantly simplifies the endoscope design and lowers its manufacturing cost. The location of the all components of the cleaning means inside the endoscope device also lowers the endoscope manufacturing cost and, moreover, improves the convenience of device control by user. Sufficiently high gas pressure supplied to the outlet nozzle as well as gas jet direction towards the optical surface provide complete cleaning of the optical surface from any patient secretion and prevent fog. Also, the high pressure gas jet is not dangerous for patient internal organs due to the noted safety means. Complete uninterrupted visualization obtained with the noted cleaning means enables shortening the endoscopy procedure duration and heightening its quality.

The safety means is the combination of gas pressure value, the nozzle dimensions, the distance between the optical surface and nozzle, the angle between gas jet direction and the optical surface, enabling safe dissipation of the gas jet after its passage over the optical surface. Moreover, additional gas jet dissipation and proximal deflection are provided with a barrier disposed in the path of gas jet movement. This safety has a low manufacturing cost and can be applied in laryngoscopes for operation in an open body cavity.

As applied to a closed body cavity, the safety means includes a return channel designed for backward movement of cleaning gas, communicated with the atmosphere by its proximal end, and having a catcher at its distal end. The catcher is designed for catching substantially the entire gas jet after its passage over said optical surface and for deflecting the gas jet into the return channel. The safety means prevents the patient internal organs from barotrauma caused by both the gas jet and excessive gas pressure in the body cavity.

In one illustrative embodiment, the safety means comprises an ejection type suction pump communicated with the return channel, disposed inside of an endoscope device, and fed by the pressurized gas source also used for feeding the nozzle. The noted type, disposition, and gas source of the suction pump provide the design simplicity and low manufacturing cost of an endoscope system. The suction pump improves the prevention of patient internal organ injury from barotrauma. Moreover, the suction pump in combination with the pressurized gas supply channel and a control valve for the control of gas consumption through the return channel allows the adjustment of gas pressure in a patient body cavity.

As applied to vacuum curettage device, the optic channel with the distal optical surface and pressurized gas supply channel with the outlet nozzle are disposed inside the tubular curettage cannula, which serves as the return channel for an endoscope cleaning system. Endoscope safety means and vacuum curettage device have one common ejection type suction pump disposed in the curettage housing and fed from the pressurized gas source of the endoscope cleaning system. The device is equipped with a pressure control means for the adjustment of required pressure in the curettage cannula. The device provides good visualization of a uterus internal wall even during curettage procedure, is entirely safe and characterized with compact, convenient, simple, and inexpensive design. This curettage device enables reduced curettage procedure duration, decreased uterus traumatization, and improved curettage quality.

DETAILED DESCRIPTION OF THE INVENTION

An explanation of the present invention is offered with reference made to the attached drawings in FIGS. 1 to 14.

Figure 1:
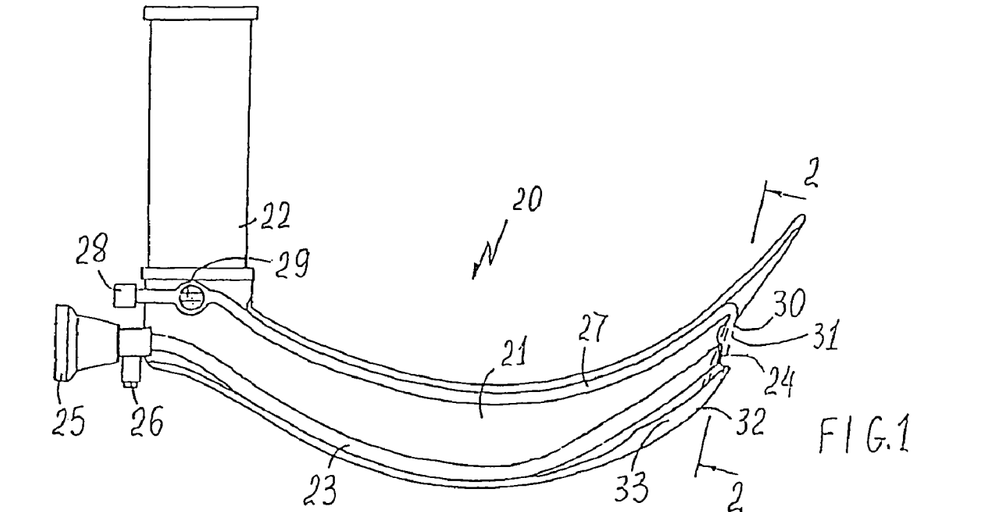
FIG. 1 shows a conceptual sketch of an intubating laryngoscope with the means for the dissipation and deflection of a gas jet.

FIG. 1 shows a laryngoscope 20 with a blade 21, a handle 22, an optic channel 23 with a distal optical surface 24, an eyepiece 25 that can be connected to a display and a connector 26 for connection to a light source. There is also a pressurized gas supply channel 27 extending along the blade 21 and having an inlet port 28 connected with a pressurized gas source (not shown), disposed beyond laryngoscope 20, a valve 29 of type ON/OF, and an outlet nozzle 30 located at a distal end of channel 27. The nozzle 30 is directed towards the optical surface 24 so that a gas jet 31 going out of the nozzle 30 touches the optical surface 24 sweeping off the dirt from it. The pressure value of gas supplied to the nozzle 30 is sufficient to convert the gas jet 31 into a high pressure gas jet capable of completely cleaning the optical surface 24 of any patient secretions and to be a single means for cleaning the optical surface 24. This pressure value provides complete cleanness of the optical surface 24, however a safety means is necessary to prevent barotrauma of patient internal organs by the gas jet 31. This safety means is the combination of the endoscope parameters enabling safe deflection and dissipation of the gas jet 31 after its passage over the optical surface 24. The noted endoscope parameters include the gas pressure value P, the nozzle 30 diameter D, the distance L between the optical surface 24 and the nozzle 30, the angle α between the optical surface 24 and adjustment of gas jet 31, and the angle β between the gas jet direction and the distal extension of an axis of the optic channel 23 distal portion. In an illustrative embodiment, the noted parameters have following values: P=40-60 psig, D=0.8-1 mm, L=2-12 mm, α=5-30°, β<70°. The angle β provides the gas jet direction proximally away from patient internal organs located in front of the optical surface 24. The other parameters provide the dissipation of the gas jet 31. Additional dissipation and proximal deflection of gas jet 31 is accomplished by a barrier 32 disposed in the path of gas jet movement after its passage over the optical surface 24 (FIG. 1, 2). The barrier 32 is also equipped with lateral deflectors 33, 34 restricting gas jet movement in side directions. Thus, the described safety means prevent barotrauma of the internal organs by the gas jet 30. However, they can only be applied in an open patient cavity, for instance in an open mouth cavity, allowing free gas exit and thereby excluding the barotrauma of internal organs by excessive pressure in a body cavity. Laryngoscope 20 provides complete cleaning of the optical surface 24 thereby reducing the intubation procedure and patient organ trauma. Moreover, it is characterized by simple, reliable, and inexpensive design due to only using gas for cleaning the optical surface 24 and the arrangement of all its components inside of the laryngoscope (with the exception of the pressure gas source and computer display).

Figure 2:
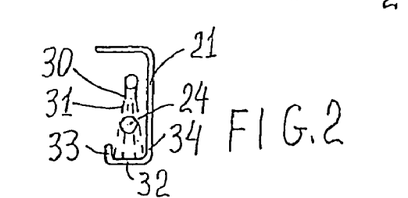
FIG. 2 shows a cross section of the laryngoscope shown in FIG. 1.
Figure 3:
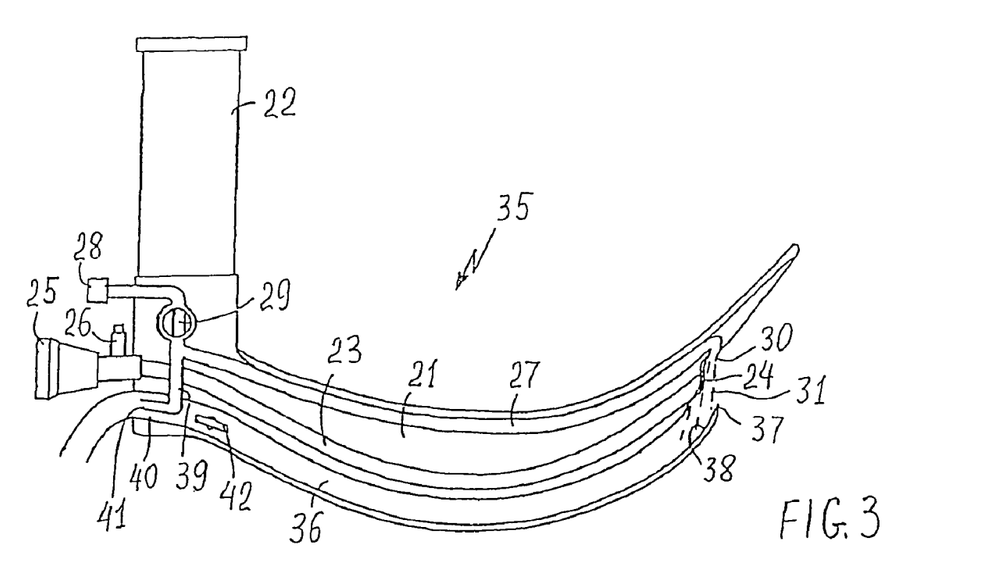
FIG. 3 shows a conceptual sketch of an intubating laryngoscope with a return channel.

The versions of the laryngoscope shown in FIGS. 1, 2, 3 have the same designations of identical details. As distinct from FIGS. 1, 2, laryngoscope 35 in FIG. 3 has a return channel 36 designed for backward movement of cleaning gas proximally from the zone of the optical surface 24. The proximal end of the return channel 36 is communicated with the atmosphere through a collector (not shown) of blood, mucus and other patient secretions. The distal end of the return channel 36 terminates in a catcher 37 for catching substantially all of the gas jet 31 after its passing over the optical surface 24 and for deflecting it into the return channel 36. The catcher 37 includes a barrier portion 38 of the return channel 36 inner wall disposed in a path of the gas jet 31 at an acute angle to it, deflecting the gas jet inwards the return channel 36 and thereby inducing backward gas movement in the return channel. In one illustrative embodiment, the laryngoscope 35 includes an ejection gas channel 39 in the form of a branch of the gas supply channel 27 disposed in the suction pipe 40, which presents a portion of the return channel 36. The ejection gas channel 39 has an ejection outlet 41 directed proximally. The noted suction pipe 40 and the ejection outlet 41 form a simplified suction pump of ejection type, which additionally induces backward gas movement in the return channel 36. This suction pump enhances laryngoscope safety means enabling operation in a closed body cavity and the removal of abundant patient secretions, for instance in the case of nasopharyngeal or oral cavity injuries.

In another illustrative embodiment, the laryngoscope 35 includes a control means for the control of gas pressure inward the body cavity. This control means presents a control valve in the form of a manually controlled throttle valve 42 allowing the change of gas consumption through the return channel 36. Valve 42 can be used, for example, for increasing the oxygen pressure in an oral cavity for the purpose of patient oxygenation, when oxygen is used as a cleaning gas.

All the components of the laryngoscope 35, with the exception of the pressurized gas source and secretion collector, are located inside the laryngoscope. All the advantages, noted for the laryngoscope 20, are inherent also in the laryngoscope 35. Both laryngoscopes can be used with a gas source of standard medical pressure, preferably oxygen piping system or pressure vessel. Therewith, the pressure of gas supplied to the nozzle 30 can be equal to the pressure in a standard medical oxygen source, approximately 50 psig.

The endoscopes, shown in FIGS. 4 to 10, have identical designations of the same details distinguished only by the first numeral.

Figure 4:
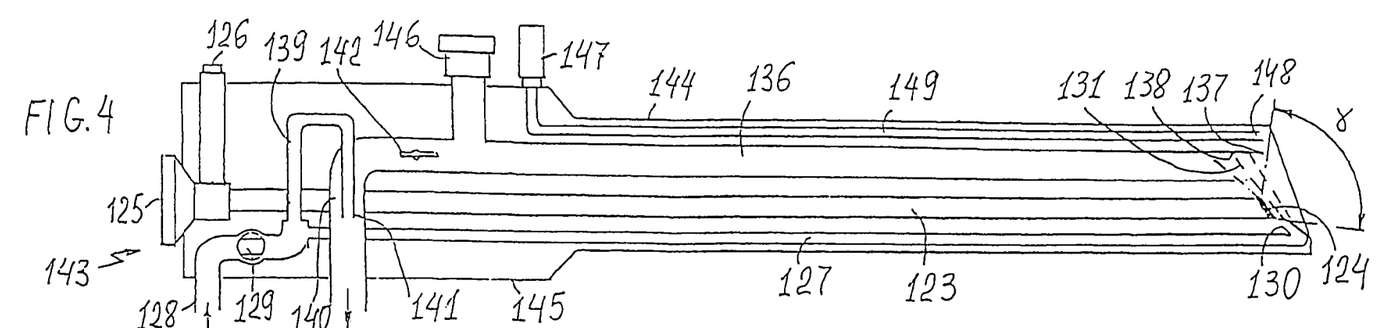
FIG. 4 shows a conceptual sketch of an endoscope with separate return channel and simplified suction pump.

The endoscope 143 in FIG. 4 comprises an elongated housing 144, a handle 145, an optic channel 123 with a distal optical surface 124, an eyepiece 125, and a connector 126 for connection of a light source (not shown). There is also a cleaning system with a pressurized gas supply channel 127 having an inlet port 128 connected with a pressure gas source (not shown), outlet nozzle 130, and a manual valve 129 of type ON/OF. The nozzle 130 is directed towards the optical surface 124 so that the gas jet 131 going out of the nozzle 130 touches the optical surface 124, cleaning from it patient secretions and fog. The pressure of gas supplied to the nozzle 130 is sufficient to convert the gas jet 131 into a high pressure gas jet capable of entirely cleaning the optical surface 124 of any patient secretions and fog, and enabling gas jet 131 to be a single means for complete cleaning the optical surface 124. As a result, the endoscope 143 provides entire visualization of patient internal organs in all cases of its application. The endoscope 143 is equipped with a safety means preventing barotraumas to patient internal organs. The safety means include a return channel 136 with a catcher 137 for catching substantially all of the gas jet 131, a safety release valve 146, and a simplified ejection type suction pump. This pump comprises an ejection gas channel 139 with an ejection outlet 141 and suction pipe 140 made as a proximal portion of the return channel 136. The operation of an identical simplified suction pump was described above as applied to the laryngoscope 35 in FIG. 3. The gas jet 131 enters the catcher 137 at an acute angle to a barrier portion 138 of the return channel 136, which deflects the gas jet into the return channel 136. The ejection suction pump induces a backward movement of cleaning gas with patient secretion and draws off the gas to the atmosphere through the return channel proximal end and a secretion collector (not shown) disposed beyond the endoscope 143. The safety release valve 146 automatically opens in the case of unforeseen closing of the control valve 142, for example because of its jamming, thereby preventing excessive pressure in the body cavity. Thus, the safety means entirely prevents barotrauma of patient internal organs caused by the gas jet 131 and excessive pressure in the body cavity. Manually controlled valve 142 allows the adjustment of the required pressure in body cavity. For this purpose, the endoscope also has an indication means including a pressure sensor 148 and indication device 147 for the measurement and indication of the gas pressure in the body cavity. In FIG. 4, the sensor 148 is the distal end of the pipe 149 communicated with usual mechanical mano-vacuumeter. The safety release valve 146 can be used for automatically maintaining required pressure in the body cavity. For this purpose, it can be set for the required pressure. After partial or entire closing of the valve 142 and increase of pressure in body cavity to an expected value, the valve 146 automatically opens maintaining the required pressure in body cavity. All the components of the endoscope 143, with the exception of the pressurized gas source and secretion collector, are located inside of the endoscope device providing compact, simple, and inexpensive design. An important merit of the endoscope 143 is the arrangement of the nozzle 130 and the catcher 137 beyond the vision field γ of the optical surface 124.

Figure 5:
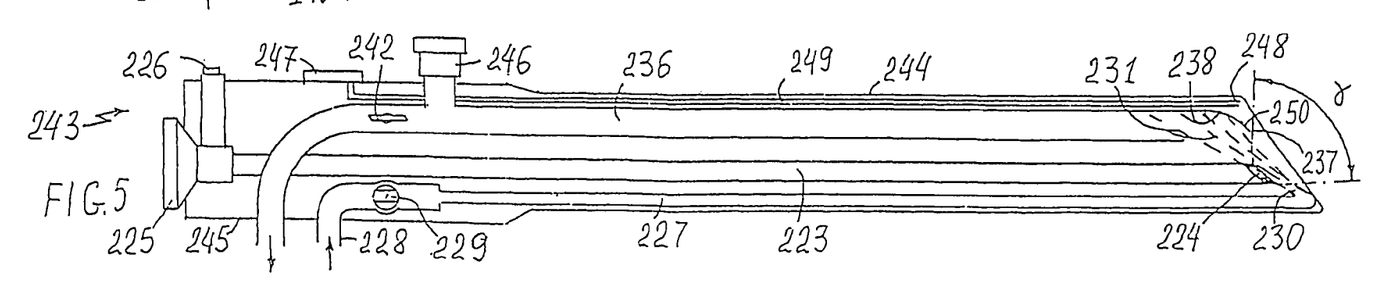
FIG. 5 shows a conceptual sketch of an endoscope with separate return channel without suction pump.
Figure 6:
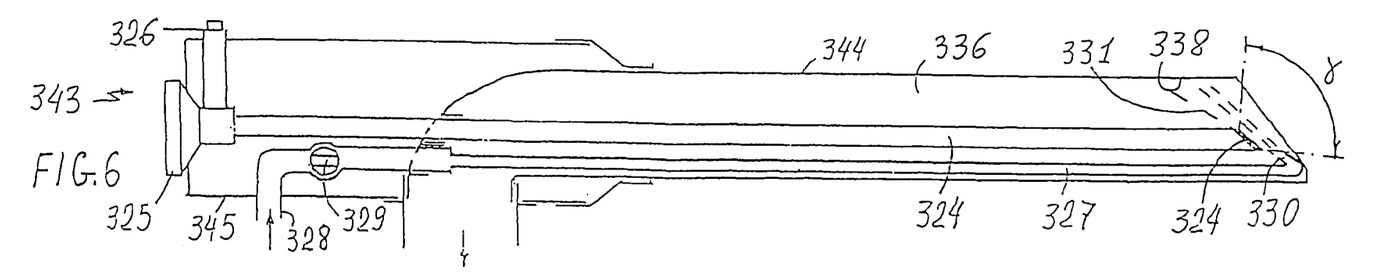
FIG. 6 shows a conceptual sketch of an endoscope with the housing serving as a return channel.

The endoscope 243 shown in FIG. 5 comprises many the same details with identical designations as in FIG. 4. Therefore, it is expedient to describe only the distinctions of the endoscope 243. This endoscope is embodied without the suction pump. The catcher 237 has the barrier portion 238 of curvilinear form smoothly deflecting the gas jet 231 into the return channel 236 with minimal losses of the dynamic thrust of the gas jet 231. As a result, the gas jet 231 induces backward gas movement in the return channel 236, thereby providing the removal of cleaning gas from the body cavity. This also allows the adjustment of required pressure in the body cavity by control valve 242. The electronic digital manometer 247 is used for the indication of body cavity pressure. The barrier portion 238 has a distal baffle 250 additionally preventing some part of the gas jet 231 from going out into a patient's cavity.

A special feature of the endoscope 343 (FIG. 6) is that its elongated housing 344 is also used as the return channel 336 providing substantial design simplification and decreasing its manufacturing cost. The gas jet 331 collides with a barrier portion 338 at an acute angle and is deflected into the return channel 336 inducing a backward gas movement in the return channel. The advantage of the return channel 336 are its relatively large dimensions and, as a consequence, low resistance to gas removal from body cavity as well as little restrictions of the vision field γ of the optical surface 324. The return channel 336 with its catcher 337 is able to provide the gas consumption through the return channel 336 substantially equal to one through the nozzle 330.

Figure 10:
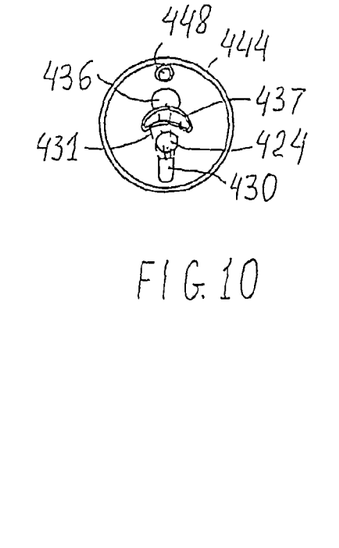
FIG. 10 shows a partial front view of the distal end of the endoscope shown in FIG. 7

The special features of the endoscope 443 (FIGS. 7 to 10) are the catcher 437 of special form, enhanced suction pump 453, and complicated pressure control system. The catcher 437 has a curvilinear form in the longitudinal section of the return channel 436 (FIG. 7) and crescent-shaped distal aperture faced to the nozzle 430 by its concave side (FIG. 10). This increases the completeness of gas jet 431 catching and lowers the resistance to gas jet entering the return channel 436. The suction pump 453 includes a separate ejection gas channel 454 and an ejection pipe in form of a short gas pipe 455 connected with the ejection gas channel 454 and having a narrowed portion 456 with side openings 457. Openings 457 are communicated with the proximal end 458 of the return channel 436. The short gas pipe 455 communicates with the secretion collector (not shown) by the pipe 459. The suction pump 453 is able to create a higher vacuum and to provide increased consumption of gas and patient secretions through the return channel 436. It can operate not only as the noted safety means, but also as an effective means for the removal of abundant secretions from patient's cavity. As distinct from the prior art, the pump 453 is characterized by simple, inexpensive design and small overall dimensions enabling its location inside of the endoscope handle 445. The pump 453 is fed from the same pressurized gas source that is used for gas supply to the nozzle 430. The pressure control system of the endoscope 443 includes the members of the cleaning means (the pressurized gas supply channel 427, the nozzle 430), the safety means (the return channel 436, the suction pump 453), and the control means. The latter includes the manually controlled first control valve 442 for the control of gas consumption through the return channel 436 and the second control valve 451 made as a valve of automatic pressure regulator 460 equipped with the means for manual setting the maintained pressure (standard widely spread pressure regulator). There is also the indication means including the pressure sensor 448 and the manometer 447 described above for the endoscopes 143, 243. The endoscope 443 has the knob 452 of the manually controlled ON/OFF valve 429 and the knob 453 of first control valve 442 (FIG. 8, 9), which are conveniently located at the right side of the handle 445. First control valve 442 and knob 453 have three following operation positions (FIG. 8) while the valve 429 is open: the first position I, wherein gas consumption through the nozzle 430 is more than one through the return channel 436; the second position II, wherein gas consumption through the nozzle 430 is equal to one through the return channel 436; the third position III, wherein gas consumption through the nozzle 430 less than one through the return channel 436. The first position enables maintenance of the required positive pressure in the patient's cavity. The second position is neutral and does not exert some action on the pressure in the patient's cavity. The third position can create the vacuum in the patient's cavity and may be used for the removal of abundant secretions from the patient's cavity. In all these positions, the endoscope 443 provides complete visualization of patient internal organs. The second control valve 451 additionally enhances the possibility of endoscope control.

FIGS. 11-14 show a vacuum curettage device 543 with a visualization means, comprising a tubular curettage cannula 544 with a distal window 571 connected with a curettage housing 545 and a curettage suction pump 553 for applying a vacuum to the cannula 544. The suction pump 553 is communicated with the cannula 544 via a suction pipe 561, a filter 562, a reservoir 568, and proximal end 567 of the cannula 544. The detachable reservoir 568 is designed for the collection of curettage products (blood, body particles), connected with the curettage housing 545 by latches 563, 564 and with the cannula proximal end 567 and the suction pipe 561 by means of sealing O-rings 565, 566. The filter 562 is permeable for gas and impermeable for curettage products to prevent the suction pump from dirtying with them. In an illustrative embodiment, the reservoir 568 is separated from the curettage housing 545 and connected with the pipes 561 and 567 by hoses (not shown). The device 543 also comprises: an optic channel 523 with a distal optical surface 524, an eyepiece 525 which can be connected to a monitor, and a connector 526 for connection with a light source (not shown); and a pressurized gas supply channel 527 having an inlet port 528 connected with a pressurized gas source (not shown), through manually controlled valve 529 of type ON/OFF, the first control valve 560 and a nozzle 530. The optic channel 523 and the pressurized gas supply channel 527 pass within the cannula 544 and, in one embodiment (FIG. 13, 14), are enclosed in a sheath 569. The presence of the sheath 569 allows the use of the members 523 and 527 along with the curettage housing 545 as a reusable device parts while the cannula 544 and the reservoir 568 are disposable. The optical surface 524 is disposed within the cannula 544 at its distal end and faces the cannula distal window 571 so that a vision field of the optical surface 524 passes through the window 571. The nozzle 530 is disposed within the cannula 544 and directed towards the optical surface 524 so that the gas jet 531 going out of the nozzle 530 touches the optical surface 524 providing its cleaning. The pressure value of gas supplied to the nozzle 530 is sufficient to completely clean the optical surface from any curettage products in spite of their abundance. As a result, the device provides complete visualization of uterus internal wall during the curettage procedure.

Figure 11:
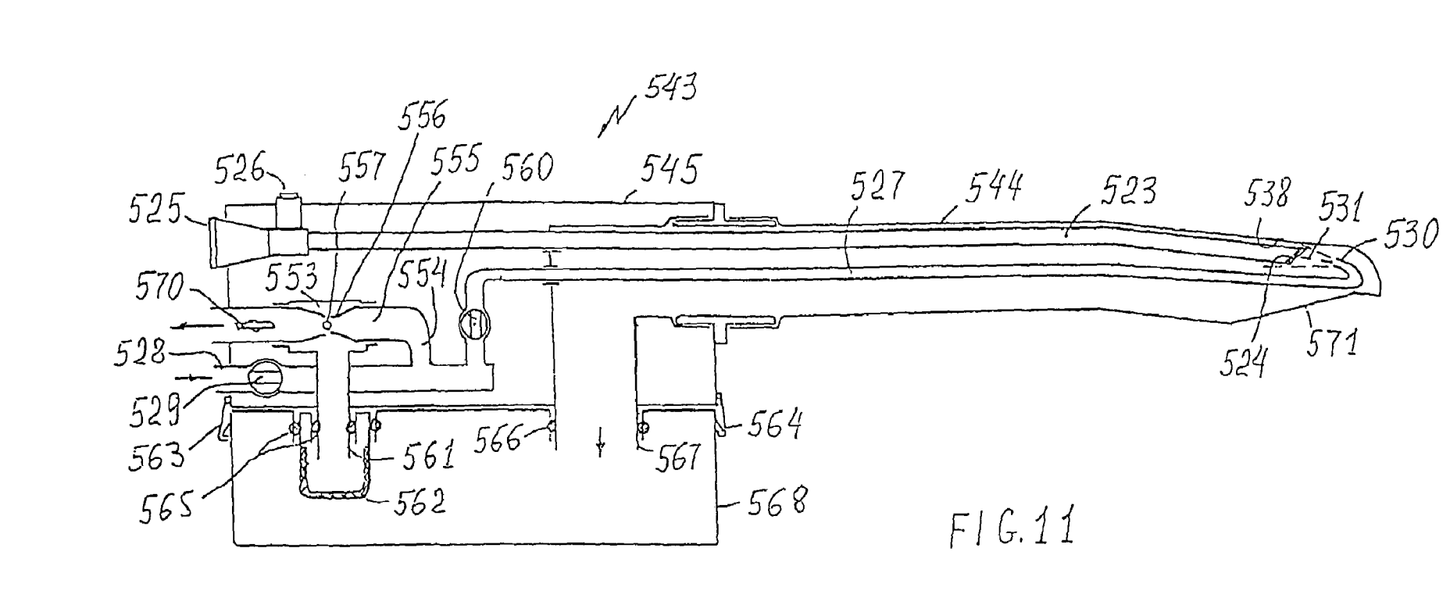
FIG. 11 shows a conceptual sketch of a vacuum curettage device with a visualization means.
Figure 12:
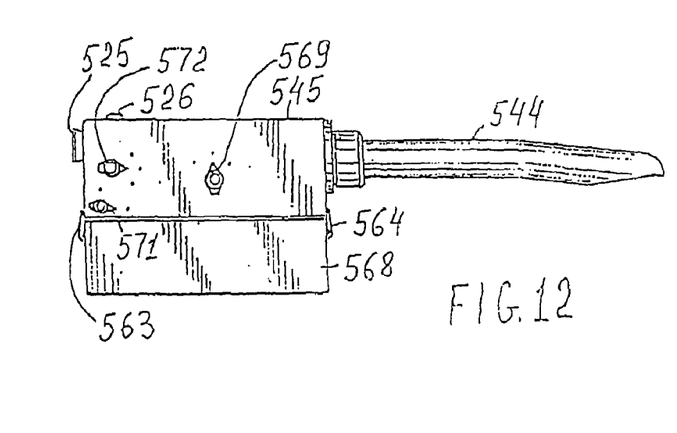
FIG. 12 shows an exterior side view of a vacuum curettage device with an endoscope.
Figure 13:
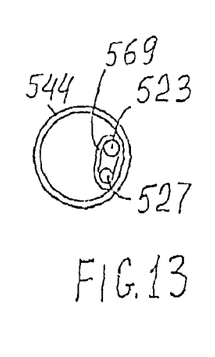
FIG. 13 shows a cross section of a vacuum curettage device cannula.
Figure 14:
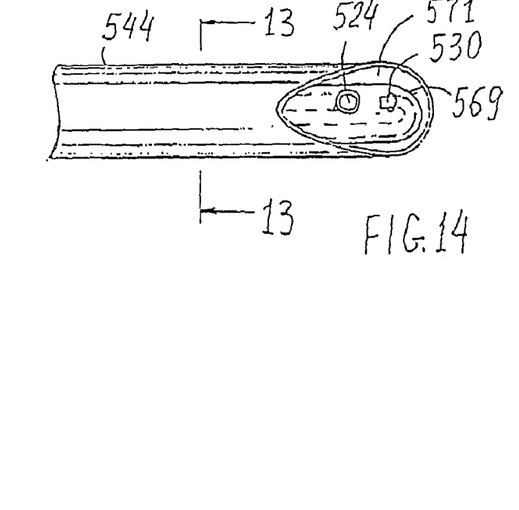
FIG. 14 shows a underside view of a curettage device distal end.

The device has a safety means preventing barotrauma of patient internal organs by gas going out of the nozzle 530. In the device 543 the curettage cannula 544 is used as a return channel of the safety means for the backward movement of cleaning gas. The curettage suction pump 553 is used also as a safety suction pump removing the cleaning gas via the return channel. The distal end of the cannula 544 has a barrier wall portion 538, which serves as a barrier disposed in the path of the gas jet 530 at an acute angle to gas jet direction deflecting the gas jet 530 into the cannula 544. Thus, the safety means entirely prevents barotraumas of patient internal organs. Note, all the components of the safety means present at the same time the components of the curettage device. As a result, substantial design simplification and lowering the device manufacturing cost are achieved. Moreover, this shows that device 543 is not simple sum of a vacuum curettage device and an endoscope.

Figure 7:
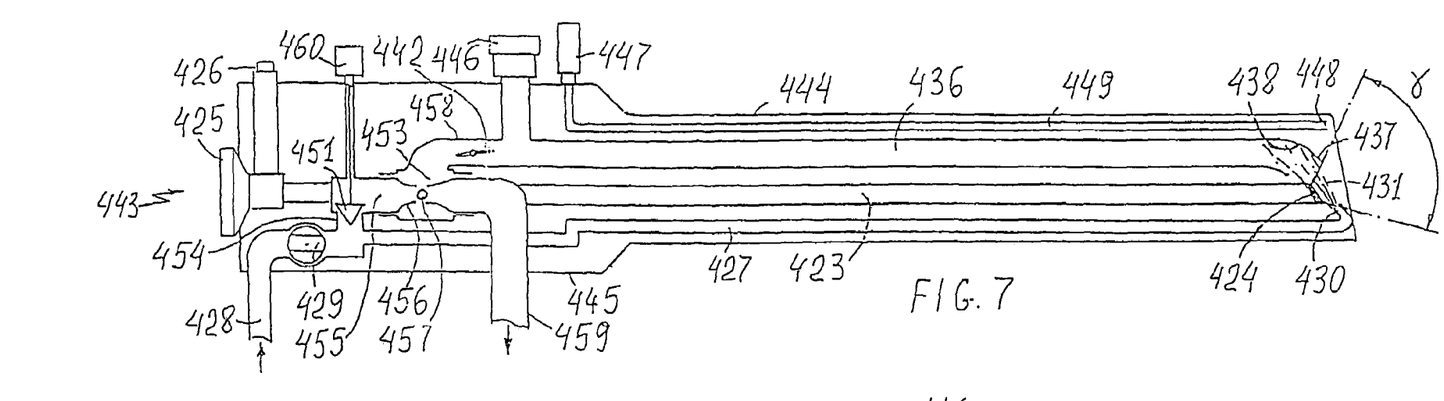
FIG. 7 shows a conceptual sketch of an endoscope with separate return channel, enhanced suction pump and the means for the adjustment of body cavity pressure.
Figure 8:
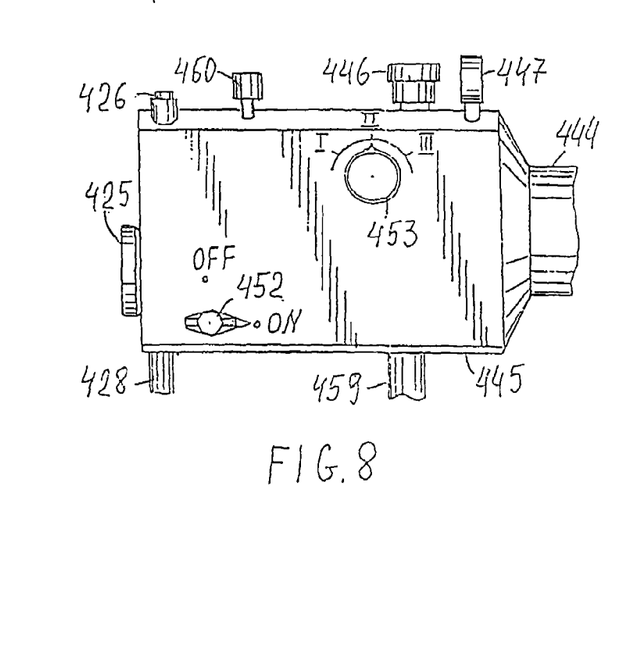
FIG. 8 shows a side elevation of the handle of the endoscope shown in FIG. 7.
Figure 9:
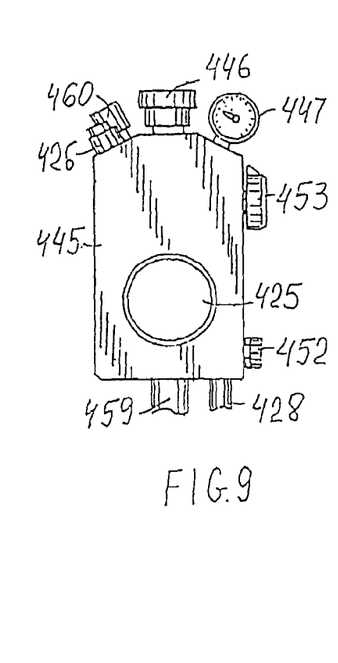
FIG. 9 shows a back view of the endoscope shown in FIG. 7.

The ejection type suction pump 553 is described above for the endoscope 443. It is simple, compact, fed from the pressurized gas source of the nozzle 530, and disposed inside of the curettage housing 545. In an illustrative embodiment (not shown), the suction pump of any type is disposed beyond the curettage device and connected with it by hoses. This design is somewhat more expensive, but can be expedient for the replacement of existent vacuum curettage devices with using an existent suction pump.

The device 543 has a pressure control means for the control of the pressure inward the cannula 544. This means includes a manually controlled valve 529 of ON/OFF type with a knob 571, first control valve 560 installed in the pressurized gas supply channel 527 and equipped with a knob 569, second control valve 570 with a knob 572 installed in the path of gas moving through the cannula 544, and suction pump 553. The device 543 is inoperative, when the valve 529 is in position OFF. Upon the curettage procedure, the valves 529 and 570 are open. The valve 560 also can be open, if the user needs the visualization during the curettage procedure. In the visualization position between or after curettage operations, the valves 529 and 560 are open and the valve 570 is open partly so that gas pressure in uterus is somewhat more than an atmospheric pressure. As a result, small excessive pressure somewhat expands uterus improving the visualization of its internal wall. The valves 529, 560, and 570 allow also the other position combinations, which are desirable for user.

In another illustrative embodiment (not shown), the valve 570 is disposed in the cannula proximal end 567 thereby protecting the reservoir 568 from the noted small excessive pressure. In another illustrative embodiment (not shown), the cannula 544 is equipped with a safety release valve, whose design, designation, and operation are identical with the valves 146, 246 in the endoscopes 143, 243 (FIG. 4, 5).

The invention claimed is:
1. An endoscope system, comprising:
an endoscope to be held by operator's hands and including,
an elongated endoscope housing having a distal end and a proximal end;
an endoscope handle affixed at said housing proximal end;
at least one optical channel designed for visualization of patient's internal organs, extending along said housing from said housing proximal end to said housing distal end, and having a distal optical surface at the distal end of said optical channel;

a cleaning system designed for cleaning said optical surface and comprising a pressurized gas supply channel which extends along said housing and has an inlet port connected with a pressurized gas source, as well as at least one outlet nozzle disposed at said housing distal end and directed towards said optical surface so that a gas jet going out of said nozzle touches said optical surface providing its cleanness, wherein the pressure value of gas supplied to said nozzle is sufficient to convert said gas jet into a high pressure gas jet capable of completely cleaning said optical surface of any patient's secretions and fog, thereby enabling said gas jet to be a single means for cleaning said optical surface, a safety means preventing the patient internal organs from barotraumas by said gas jet going out of said nozzle, wherein all components of said cleaning system and said safety means are disposed inside of said endoscope, with the exception of said pressurized gas source.

2. The endoscope system of claim 1, wherein said safety means is made as a dissipation means designed for safe dissipation and deflection of said gas jet going out of said nozzle.

3. The endoscope system of claim 2, wherein said cleaning system and dissipation means provide for the combination of endoscope parameters enabling safe dissipation and deflection of said gas jet after its passage over said optical surface and including a gas pressure value of 40-60 psig, the diameter of said nozzle being between 0.8-1.0 mm, the distance between said optical surface and said nozzle being between 2-12 mm, the angle between a direction of said gas jet and said optical surface being between 5-30°.

4. The endoscope system of claim 2, wherein said dissipation means includes a barrier disposed in a path of said gas jet movement after its passage over said optical surface, wherein said barrier has a surface, which partly dissipates said gas jet and partly deflects it proximally, and also includes lateral deflectors restricting said gas jet movement in the side directions.

5. The endoscope system of claim 4, wherein an axis of said nozzle is positioned at an acute angle to the surface of said barrier.

6. The endoscope system of claim 1, wherein said safety means includes a return channel having a distal end and a proximal end and designed for backward movement of cleaning gas proximally from a zone of said optical surface after gas passage over said optical surface.

7. The endoscope system of claim 6, wherein said return channel proximal end is communicated with the atmosphere through a collector of blood, mucus and other patient's secretions.

8. The endoscope system of claim 6, wherein said return channel is a separate channel extended along said housing.

9. The endoscope system of claim 6, wherein said return channel distal end is provided with a catcher for substantially entirely catching said gas jet after its passage over said optical surface and for entirely deflecting said gas jet into said return channel.

10. The endoscope system of claim 9, wherein said catcher includes a barrier portion of an inner wall of said return channel distal end disposed in the way of said gas jet and adapted to the deflection of said gas jet into said return channel.

11. The endoscope system of claim 10, wherein said catcher further serves to induce said gas backward movement in said return channel as a result of said barrier portion being disposed at an acute angle to the direction of said gas jet.

12. The endoscope system of claim 10, wherein said barrier portion has a distal baffle additionally preventing some part of said gas jet from going out into the patient's cavity.

13. The endoscope system of claim 10, wherein said barrier portion is a portion of said return channel wall extended distally relative to said return channel distal end.

14. The endoscope system of claim 10, wherein said catcher includes a crescent-shaped aperture facing side nozzle by its concave side.

15. The endoscope system of claim 6, wherein said safety means comprises a suction pump of ejection type inducing said backward gas movement in said return channel, communicated with said return channel, disposed inside of said endoscope, including an ejection pipe and an ejection gas channel, and said ejection gas channel is communicated with said pressurized gas source.

16. The endoscope of claim 15, wherein a portion of said return channel is used as said ejection pipe having an inwardly located ejection outlet directed in the direction of said backward gas movement and connected with said ejection gas channel.

17. The endoscope system of claim 16, wherein said ejection gas channel is a side branch of said gas supply channel.

18. The endoscope system of claim 16, wherein said ejection gas channel is a channel separate from said gas supply channel.

19. The endoscope system of claim 16, wherein there is a pressure control system for the control of pressure the patient's cavity, comprising said cleaning means, said safety means, and a control means.

20. The endoscope system of claim 19, wherein said pressure control system is entirely disposed inside of said endoscope.

21. The endoscope system of claim 19, wherein said control means includes a control valve for the control of gas consumption through said return channel.

22. The endoscope system of claim 21, wherein said control valve has at least three following positions: the first position, wherein a gas consumption through said nozzle is more than one through said return channel; the second position, wherein gas consumption through said nozzle is equal to one through said return channel; the third position, wherein gas consumption through said nozzle is less than one through said return channel.

23. The endoscope system of claim 22, wherein said control valve is installed in said return channel.

24. The endoscope system of claim 23, wherein said control valve is a throttle valve provided with a manual drive.

25. The endoscope system of claim 21, wherein said control valve is installed in said ejection gas channel.

26. The endoscope system of claim 25, wherein said control valve is a valve of automatic pressure regulation provided with a means for manually setting the maintained pressure.

27. The endoscope system of claim 19, wherein there is an indication means for the measurement and indication of the pressure in the patient's cavity.

28. The endoscope system of claim 27, wherein said indication means includes a pressure sensor disposed at said housing distal end and an indicating device disposed at said handle.

29. The endoscope system of claim 15, wherein said ejection pipe is a separate short gas pipe having first and the second ends connected with said ejection gas channel by said first end and having a narrowed portion with side openings, which are communicated with said return channel proximal end.

30. The endoscope system of claim 29, wherein said ejection pipe second end is communicated with a secretion collector disposed beyond said endoscope.

31. The endoscope system of claim 1, wherein there is a safety release valve operating automatically to prevent excessive pressure in the patient's cavity.

32. An endoscope to be held by an operator's hands, comprising:
  an elongated endoscope housing having a distal end and a proximal end,
  an endoscope handle affixed at said housing proximal end,
  at least one optical channel designed for the visualization of a patient's internal organs, extending along said housing from said housing proximal end to said housing distal end, and having a distal optical surface at a distal end of said optical channel,
  a cleaning system designed for cleaning said optical surface and comprising a pressurized gas supply channel which extends along said housing and has an inlet port connected with a pressurized gas source located beyond said endoscope, and at least one outlet nozzle disposed at said housing distal end and directed towards said optical surface so that a gas jet going out of said nozzle touches said optical surface providing its cleanliness, wherein
  the pressure value of gas supplied to said nozzle is sufficient to convert said gas jet into a high pressure gas jet capable of completely cleaning said optical surface of any patient's secretions fog, thereby enabling said gas jet to be a single means for cleaning said optical surface,
  all the components of said cleaning system are disposed inside of said endoscope, with the exception of said pressure gas source,
  a safety means preventing the patient internal organs from barotrauma by said gas going out of said nozzle and comprising
  a return gas channel for the backward movement of cleaning gas proximally from said housing distal end,
  a suction pump of ejection type inducing said backward gas movement, fed from said pressurized gas source and disposed at an assembly of said endoscope handle and endoscope housing,
  a pressure control system designed for the control of the pressure into the patient's cavity and including
  said cleaning means, which simultaneously serves both for cleaning said optical surface and as a component of said pressure control system supplying gas into the patient's cavity,
  said safety means, which simultaneously serves both preventing patient from barotrauma and as a component of said pressure control system removing gas from the patient's cavity,
  and a control means.

33. The endoscope of claim 32, wherein said return channel distal end is provided with a catcher for catching said gas jet after its passage over said optical surface and for deflecting it into said return channel.

34. The endoscope of claim 32, wherein said suction pump includes an ejection pipe and an ejection gas channel.

35. The endoscope of claim 34, wherein said control means includes a control valve designed for the control of gas pressure in the patient's cavity and having at least three following positions: the first position, wherein gas consumption through said nozzle is more than one through said return channel; the second position, wherein gas consumption through said nozzle is equal to one through said return channel; the third position, wherein gas consumption through said nozzle is less than one through said return channel.

36. The endoscope of claim 35, wherein said control valve is installed in said return channel and is a throttle valve provided with a manual drive.

37. The endoscope of claim 35, wherein said control valve is installed in said ejection gas channel and is a valve of automatic regulation provided with the means for manual setting the maintained pressure.

38. The endoscope of claim 35, wherein said control valve is installed in said gas supply channel.

39. An endoscope system, comprising:
  an endoscope to be held by operator's hands including
  an elongated endoscope housing having a distal end and a proximal end;
  an endoscope handle affixed at said housing proximal end;
  at least one optical channel designed for the visualization of patient internal organs, extending along said housing from said housing proximal end to said housing distal end, and having a distal optical surface at the distal end of said optical channel;
  a cleaning system designed for cleaning said optical surface and comprising
  a pressurized gas supply channel which extends along said housing and has
  an inlet port connected with a pressurized gas source,
  and at least one outlet nozzle disposed at said housing distal end and directed towards said optical surface to clean it,
  a return gas channel for the backward movement of gas proximally from said distal housing end,
  a suction pump inducing said backward gas movement,
  a pressure control system designed for the control of the pressure into the patient's cavity and including said pressurized gas supply channel, said nozzle, said pressurized gas source, said return channel, said suction pump and a control means, which includes a control valve having at least two following positions: the first position, wherein gas consumption through said nozzle is more than one through said return channel; the second position, wherein gas consumption through said nozzle is equal to one through said return channel.

40. The endoscope system of claim 39, wherein the pressure value of gas supplied to said nozzle is sufficient to convert said gas jet into a high pressure gas jet capable of completely cleaning said optical surface of any patient's secretion and fog, thereby enabling said gas jet to be a single means for cleaning said optical surface.

41. The endoscope system of claim 40, wherein said suction pump is of ejection type and fed from said pressurized gas source.

42. The endoscope system of claim 40, wherein a distal end of said return channel is provided with a catcher for catching said gas jet after its passage over said optical surface and for deflecting it into said return channel.

43. The endoscope system of claim 40, wherein there is a safety means preventing the patient's internal organs from barotraumas by gas going out of said nozzle and comprising said return gas channel and said suction pump.

44. The endoscope system of claim 39, wherein all the components of said cleaning system and said safety means are disposed inside of said endoscope, with the exception of said pressurized gas source disposed beyond said endoscope.

45. The endoscope system of claim 39, wherein said control valve is installed in said return channel and is a throttle valve provided with a manual drive.

46. An endoscope to be held by operator's hands, comprising:
- an elongated endoscope housing having a distal end and a proximal end,
- an endoscope handle affixed at said housing proximal end,
- at least one optical channel designed for the visualization of patient internal organs, extending along said housing from said housing proximal end to said housing distal end, and having a distal optical surface at the distal end of said optical channel,
- a cleaning system designed for cleaning said optical surface and comprising
- a pressurized gas supply channel which extends along said housing and has an inlet port connected with a pressurized gas source disposed beyond said endoscope,
- and at least one outlet nozzle disposed at said housing distal end, directed towards said optical surface so that a gas jet going out of said nozzle touches said optical surface providing its cleanliness, wherein
- the pressure value of gas supplied to said nozzle is sufficient to convert said gas jet into a high pressure gas jet capable of completely cleaning said optical surface of any patient's secretion and fog, thereby enabling said gas jet to be a single means for cleaning said optical surface,
- a safety means preventing a patient's internal organs from barotrauma by said gas jet and including
- a gas return channel for the backward movement of cleaning gas proximally from said distal housing distal end after gas passage over said optical surface, extending along said housing and having
- a receiving opening of a distal end of said return channel, which is disposed in the path of said gas jet after its passage over said optical surface,
- and an inner portion of said return channel collided with said gas jet at an acute angle less than 45° deflecting gas into said return channel and thereby inducing said backward movement of cleaning gas inside said return channel, all the components of said cleaning system and said safety means are disposed inside of said endoscope, with the exception of said pressurized gas source.

47. The endoscope of claim 46, wherein said return channel is a separate channel extended along said housing.

48. The endoscope of claim 46, wherein said return channel inner portion, in longitudinal section of said return channel, has curvilinear form enabling smooth deflecting of said gas jet into said return channel with minimal losses of dynamic thrust.

49. The endoscope of claim 46, wherein said return channel inner portion, in transverse section, has a crescent-shaped form facing said nozzle by its concave side.

50. The endoscope of claim 46, wherein there is the equality of gas consumption through said nozzle and said return channel.

51. A vacuum curettage device to be held by operator's hands and provided with a visualization means, comprising:
- a curettage device housing,
- a tubular curettage cannula having a distal open window and a proximal end connected with said curettage device housing,
- a curettage suction pump for applying vacuum to said cannula,
- at least one optical channel designed for the visualization of uterus internal surfaces, extending along said curettage device, and having a distal optical surface disposed at the distal end of said cannula,
- a cleaning system designed for cleaning said optical surface and comprising a pressurized gas supply channel extending along said curettage device and having an inlet port connected with a pressurized gas source,
- and at least one outlet nozzle disposed at said cannula distal end, directed towards said optical surface so that a gas jet going out of said nozzle touches said optical surface providing its cleanliness, wherein a pressure value of gas supplied to said nozzle is sufficient to convert said gas jet into a high pressure gas jet capable of completely cleaning said optical surface of any patient's secretions and fog and to be a single means for cleaning said optical surface,
- a safety means preventing the patient internal organs from barotraumas by gas going out of said nozzle,
- at least first control valve capable of controlling the gas supply into said pressurized gas supply channel and allowing the gas supply into said pressurized gas supply channel in the curettage regime to provide the uterus visualization in this regime.

52. The vacuum curettage device of claim 51, wherein said distal optical surface is facing said cannula distal window and a vision field of said optical surface passes through said distal window.

53. The vacuum curettage device of claim 52, wherein said safety means includes a return gas channel for the backward movement of cleaning gas proximally from said cannula distal end after gas passage over said optical surface, a safety suction pump inducing said backward gas movement.

54. The vacuum curettage device of claim 53, wherein said cannula serves also as said return channel and said curettage suction pump serves also as said safety suction pump.

55. The vacuum curettage device of claim 54, wherein said suction pump is of ejection type, fed from said pressurized gas source and disposed in said curettage housing.

56. The vacuum curettage device of claim 54, wherein said suction pump is disposed beyond said vacuum curettage device.

57. The vacuum curettage device of claim 51, wherein there is a pressure control means designed for the control of the pressure into said cannula and including said first control valve installed in the path of gas moving through said pressurized gas supply channel and at least one second control valve installed in a path of gas moving through said cannula and said suction pump, as well as, preferably, a common valve of ON/OFF type at said pressurized gas inlet port.

58. The vacuum curettage device of claim 57, wherein there are following positions of said valves: an inoperative position, wherein said common valve is closed (position OFF); a curettage position, wherein said common valve and said second control valve are open; a visualization position, wherein said common and said first control valves are open.

59. The vacuum curettage device of claim 58, wherein said curettage position and visualization position act simultaneously providing the uterus visualization during the curettage operation regime.

60. The vacuum curettage device of claim 58, wherein, in said visualization position, the second control valve is open partly so that the gas pressure in the uterus is more than atmospheric pressure enabling uterus expansion for its convenient visualization.

61. A laryngoscope system, comprising:
a laryngoscope to be held by operator's hands and including,
an elongated laryngoscope housing having a distal end and a proximal end,
laryngoscope handle affixed at said housing proximal end,
at least one optical channel designed for the visualization of patient internal organs, extending along said housing from said housing proximal end to said housing distal end, and having
a distal optical surface at the distal end of said optical channel,
a cleaning system designed for cleaning said optical surface and comprising
a pressurized gas supply channel which extends along said housing and has
an inlet port connected with a pressurized gas source and at least one outlet nozzle disposed at said housing distal end, directed towards said optical surface so that a gas jet going out of said nozzle touches said optical surface providing its cleanliness, wherein a pressure value of gas supplied to said nozzle is sufficient to convert said gas jet into a high pressure gas jet capable of completely cleaning said optical surface of any patient's secretion and fog, thereby enabling said gas jet to be a single means for cleaning said optical surface,
a safety means preventing the patient internal organs from barotrauma by said gas going out of said nozzle and operable as a dissipation means designed for safe dissipation and deflection of said gas jet going out of said nozzle, all the components of said cleaning system and said safety means are disposed inside of said laryngoscope, with the exception of said pressure gas source.

62. The laryngoscope system of claim 61, wherein said dissipation means includes a barrier disposed in the path of said gas jet movement after its passage of said optical surface; said barrier has a surface, which partly dissipates said gas jet and partly deflects it proximally, and includes also lateral deflectors restricting said gas jet movement in the side directions, and the axis of said nozzle is positioned at acute angle to said barrier surface.

* * * * *